United States Patent

Bauer et al.

Patent Number: 5,388,581
Date of Patent: Feb. 14, 1995

[54] EXTRACORPOREAL THERAPY APPARATUS

[75] Inventors: Edgar Bauer, Kraistal; Werner Krauss, Knittlingen; Michael Meyer, Bruchsal; Joachim Fladl, Oberderdingen, all of Germany

[73] Assignee: Richard Wolf GmbH, Knittlingen, Germany

[21] Appl. No.: 255,578

[22] Filed: Jun. 8, 1994

Related U.S. Application Data

[63] Continuation of Ser. No. 966,283, Oct. 26, 1992, abandoned.

[30] Foreign Application Priority Data

Oct. 25, 1991 [DE] Germany .................. 4135328

[51] Int. Cl.[6] ............................... A61B 17/22
[52] U.S. Cl. .................... 128/653.1; 128/660.03; 601/3; 601/4; 378/162; 378/175; 378/205
[58] Field of Search ............. 128/653.1, 660.03; 601/2–4; 607/97; 378/162, 175, 205

[56] References Cited

U.S. PATENT DOCUMENTS 5,144,953  9/1992  Wurster et al. ............ 128/24 EL
5,222,484  6/1993  Krauss et al. ............. 128/24 EL

FOREIGN PATENT DOCUMENTS

3919083C1  6/1990  Germany .
9017444    4/1991  Germany .
4007669A1  9/1991  Germany .

Primary Examiner—Ruth S. Smith
Attorney, Agent, or Firm—Cohen, Pontani, Lieberman, Pavane

[57] ABSTRACT

The therapy apparatus described for treating concretions and tissue in the body of a patient by means of sound waves comprises a sound wave generator and an available X-ray device for locating an object for therapy, wherein the therapy apparatus has a spot film device. The spot film device is arranged within the axial passage of an X-ray cone for the available X-ray device attached to the sound wave generator and with its central longitudinal axis aligned with the focus thereof to be able to precisely adjust and fix a known X-ray device available to the therapy apparatus relative to the therapy apparatus quickly and safely.

11 Claims, 7 Drawing Sheets

EXTRACORPOREAL THERAPY APPARATUS

This is a continuation of U.S. application Ser. No. 07/966,283, filed Oct. 26, 1992, now abandoned.

BACKGROUND OF THE INVENTION a) Field of the Invention

The invention relates to an extracorporeal therapy apparatus for treating concretions and tissue by means of sound waves in the body of a patient, having a generator device for producing the sound waves, having a spot film device and using an available X-ray device for locating an object for therapy.

b) Description of the Prior Art

European patent application no. 0 402,584 describes a therapy apparatus of the type mentioned above in the form of a lithotripter. A spot film device consisting of a substrate of X-ray negative material and several spot film markers of X-ray positive material embedded therein, is mounted externally and directly on the head of a shock wave generator. Four spot film markers or reference points are provided, and in each case two spot film markers on the substrate each define one spot film line, so that two intended spot film lines are defined. This shock wave generator thus equipped is used in conjunction with an available X-ray device of C-arm construction. The two spot film lines intersect at a point which has to be brought into line with the focal point of the shock wave generator and where the object for therapy in the patient is adjusted later.

Although this spot film device makes for easier adjustment of the X-ray device onto the focus of the shock wave generator and hence onto a concretion in the body of a patient, carrying out adjustment and hence location using this spot film device is nevertheless still awkward and unsafe. After coarse adjustment of the available X-ray device onto the spot film device, initially the bundle of rays from the X-ray device must be aligned with the first spot film line of the spot film device. Then a hypothetical focal point on the shock wave generator must be fixed on a first line corresponding to the first spot film line on the screen of a monitor and then the object for therapy in the patient also visible on the screen must be adjusted onto the hypothetical focus. Several X-ray images are taken to obtain this result. The third spatial coordinate of the therapy point in the patient with respect to the hypothetical focus can be seen by pivoting the X-ray device into the second spot film line of the spot film device. By conventional adjustment of the operating table, on which the patient is situated, the object for therapy in the patient is then adjusted into the final hypothetical focal point; this means that the true focus of the shock wave generator is then in fact aligned with the object for therapy. Several X-ray images are also taken for this result. Overall the X-ray load is thus relatively high. Furthermore, the spot film device is unprotected and may itself be easily displaced, for example by bumping.

German Offenlegungsschrift 4,007,669 describes a lithotripter, the shock wave generator of which is provided with an X-ray device, the ray axis of which coincides with the focus of the generator and which consists of an X-ray cone and the actual X-ray source. German Offenlegungsschrift 3,916,093 describes a further lithotripter which is also rigidly connected to an X-ray device of C-arm support construction which can be adjusted in three spatial coordinates. These lithotripters have a special C-arm for the X-ray device which is always rigidly connected to the shock wave generator.

The object of the invention consists in improving an extracorporeal therapy apparatus of the type mentioned in the introduction so that it is possible to position an available X-ray device with respect to the therapy apparatus for the purpose of more rapid X-ray location of the patient's object for performing the therapy quickly, safely and simply.

SUMMARY OF THE INVENTION

The present invention meets this object with an extracorporeal therapy apparatus for treating concretions and tissue by means of sound waves in the body of a patient, having a short wave generator device for producing the sound waves, having a spot film device and using an available X-ray device for locating an object for therapy, characterised in that the spot film device is assigned to the passage of an X-ray cone, attached to the short wave generator device and having its central longitudinal axis aligned with the focus thereof, for the available X-ray device which can be releasably fixed to the short wave generator device.

The alignment of the available X-ray devices of C-arm construction used in clinics, in addition to other tasks, for example also for lithotripsy and tissue treatment, with the focus of the shock wave generator and hence with the concretion or tissue of the patient to be treated by means of ultrasound, as well as X-ray location of the object for therapy, is made considerably easier using this solution. This results from the fact that the central longitudinal axis of the X-ray cone extends through the focus of the short wave generator due to the fixed assembly of this cone on the ultrasound short wave generator from the beginning, and the single spot film line of the spot film device of the X-ray cone now lying on the inside coincides with the central longitudinal axis thereof, and that the X-ray device is pivoted confocally with the shock wave short wave generator because the C-arm support supporting the X-ray device is releasably fixed to the shock wave short wave generator, and the C-arm support and the shock wave short wave generator are pivoted together as a unit. A separate adjustment of the X-ray apparatus of C-arm construction to a second spot film line is thus omitted. The spot film markers of the spot film device always appear in alignment on the observation monitor for the correct setting of the X-ray device, and the object for therapy also visible on the monitor may be adjusted easily into the spot film markers shown by means of the patient operating table which can be adjusted in the three spatial coordinates X, Y and Z. The main axis of the X-ray beam from the available X-ray device is aligned in simple manner with the focus of the shock wave generator using the arrangement according to the invention of the spot film device protected within the X-ray cone, so that the spot film device represents the exact geometrical location of the focus of the shock wave generator on the X-ray monitor in any projection direction after adjustment and fixing the X-ray device on the shock wave generator.

A preferred embodiment of the spot film device comprises two discs of X-ray negative material arranged parallel to one another and at a distance from one another in the interior of the X-ray cone and spot film markers of X-ray positive material provided on or in the discs, wherein the centres of the discs preferably lie on the central axis of the X-ray cone.

Preferably, the spot film markers consist of channels representing geometrical figures formed in the discs and of an X-ray positive liquid which can be pumped through the channels. The X-ray positive liquid is suitably an X-ray contrast agent, mercury or a mixture of alcohol and an X-ray contrast agent.

This spot film device has a simple construction and its X-ray visibility may be limited by pumping the X-ray positive liquid out of the channels of the spot film markers.

The spot film device may comprise two geometrically-shaped spot film figures of solid X-ray positive material at a distance from one another and parallel to one another.

The spot film figures may consist of metal components and can be pivoted in and out of the ray path of the X-ray device passing through the X-ray cone. The therapy apparatus of the invention suitably has a shock wave generator of dome construction, characterised in that the X-ray cone is arranged to be fixed in the center of the dome component or offset at an angle thereto, such that the spot film line of the spot film device extends through the focus of the shock wave generator.

It is preferred that an ultrasound scanner can be inserted in the X-ray cone for ultrasound location and can be rotated by motor and that it is designed to be height-adjustable.

The therapy apparatus may also include a patient operating table with a device for its adjustment in three spatial coordinates, characterised in that the adjusting device supporting the table comprises two lower, surface-forming locating units which can be adjusted in the horizontal X-Y-coordinates and a lifting unit supporting the table plate arranged thereon.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed. In the drawings.

DESCRIPTION OF THE PREFERRED EMBODIMENTS

Figure 1:
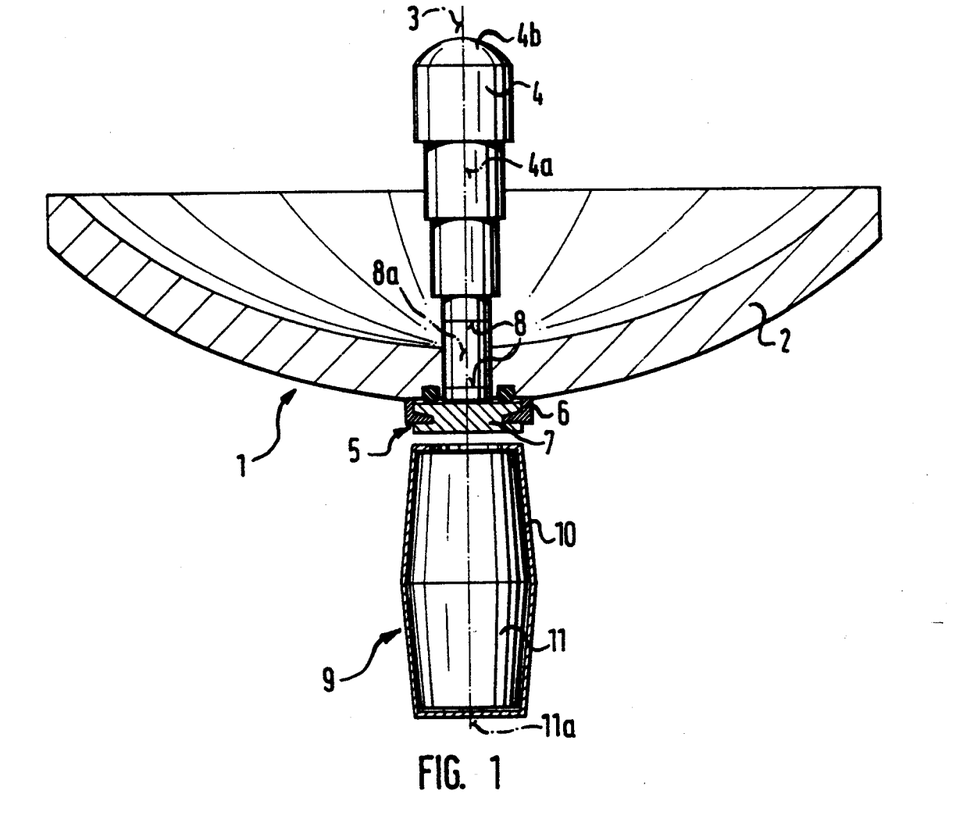
FIG. 1 shows a simplified axial section through a shock wave generator and an only partly shown C-arm support, wherein the short wave generator and the C-arm support are adjusted with respect to one another together as a unit.

FIG. 1 shows an extracorporeal therapy apparatus generally designated 1 for producing sound waves for the purpose of treating a patient's object for therapy, for example concretions or tissue. Treatment using sound waves usually takes place by means of ultrasound shock waves for concretions, and for tissue, for example tumors, by means of transient high-energy ultrasound pulses for mechanical shredding of tissue or by means of high-energy ultrasound operated continuously or in bursts for thermal destruction of tissue.

The therapy apparatus 1 comprises a known sound wave short wave generator 2 of dome construction, for example for ultrasound shock waves. An X-ray cone 4 is connected rigidly to the short wave generator in the center of the generator 2 along its central axis indicated by the dot-and-dash line 3. This X-ray cone 4 is preferably designed to be longitudinally adjustable, as indicated for example in German Offenlegungsschrift 4,007,669, so that more detailed explanation of its construction is superfluous. The lower region of the X-ray cone 4 is sealed in air-tight manner by means of a closure device 5 comprising a bayonet mounting part 6 attached to the short wave generator 2 and a closure plate part 7 arranged to be removable therefrom. The plate part 7 is permeable to X-rays. The longitudinal axis 4a of the X-ray cone 4 coincides with the central axis 3 of the short wave generator 2.

The lower end region of the X-ray cone 4 facing the generator 2 is provided with a spot film device 8 which defines a spot film line 8a and which is shown in more detail in FIGS. 2 to 5.

Figure 6:
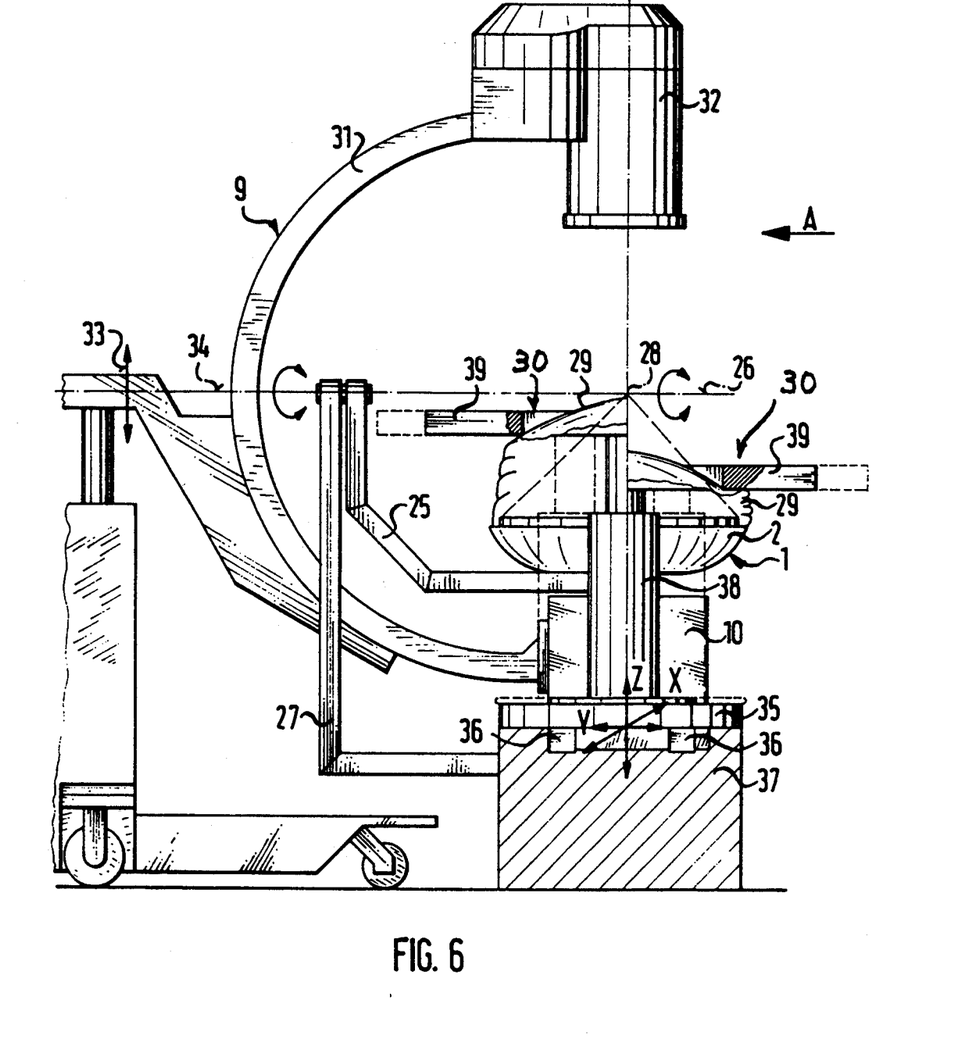
FIG. 6 shows an end view of a whole arrangement comprising lithotripter, patient operating table and available X-ray device.
Figure 8:
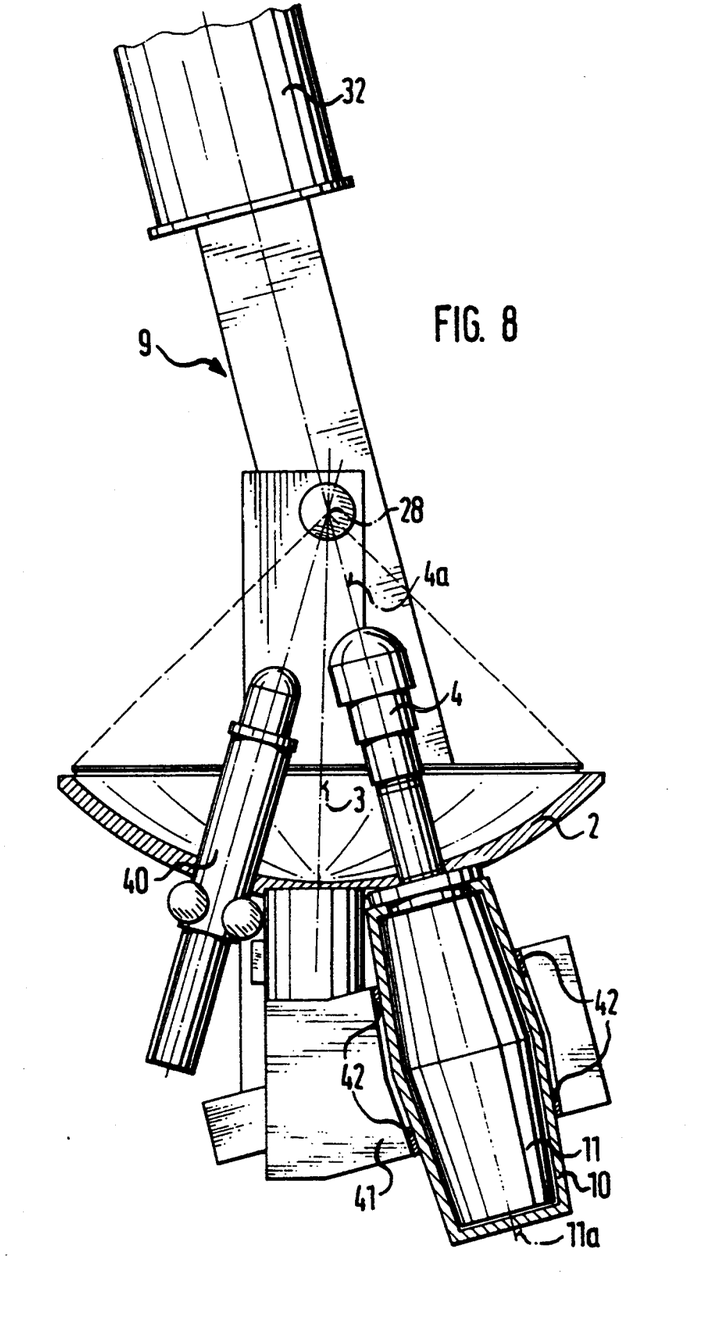
FIG. 8 shows a representation of a further embodiment of the shock wave generator and available C-arm support forming a fixed unit.

An available X-ray device 9 of C-arm construction, which can be seen more clearly in FIGS. 6 and 8, is positioned and fixed below the shock wave generator 2 if X-ray location of a concretion in a patient is to be carried out. For a better overview, the shock wave generator 2 is only shown partially in FIG. 1, that is there is not shown any flexible, upper space limit or a liquid medium to transfer the sound waves destroying the concretion. However, these features regarding construction and function are known to the expert. Of the X-ray device 9, also shown only partly in FIG. 1, only one mounting 10 and an X-ray emitter 11 mounted therein is shown in this figure.

The X-ray device 9 of C-arm construction can be releasably connected to the shock wave generator 2 below the latter, and in particular such that the central ray axis 11a of the X-ray emitter 11 of the device 9 is aligned to be flush with the spot film line 8a of the spot film device 8. For this, for example the shock wave generator 2 is provided with retaining, adjusting and fixing means such as shown schematically in FIG. 8 at 41, so that the X-ray emitter 11 can be adjusted relative to the generator 2 and then fixed. After fixing, the X-ray device 9 and the shock wave generator 2 form a unit and together can be pivoted confocally about the focus of the shock wave generator 2.

Figure 2:
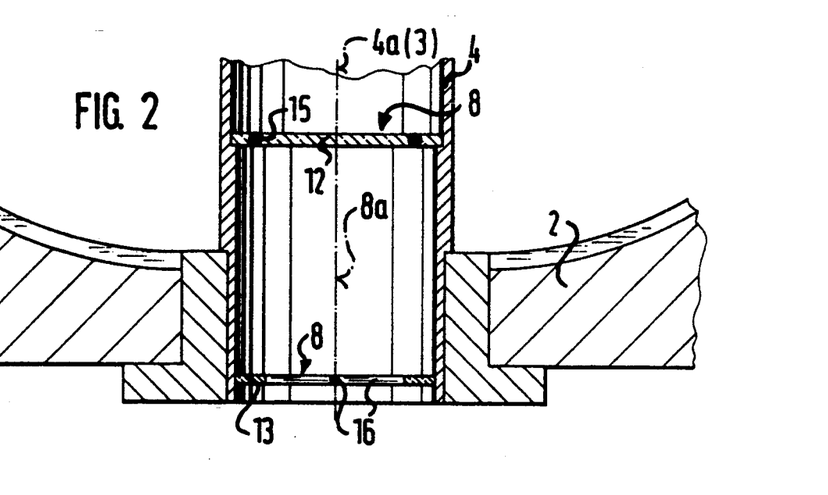
FIG. 2 shows an axial, enlarged partial section of the shock wave generator according to FIG. 1 with a first embodiment of a spot film device.
Figure 3:
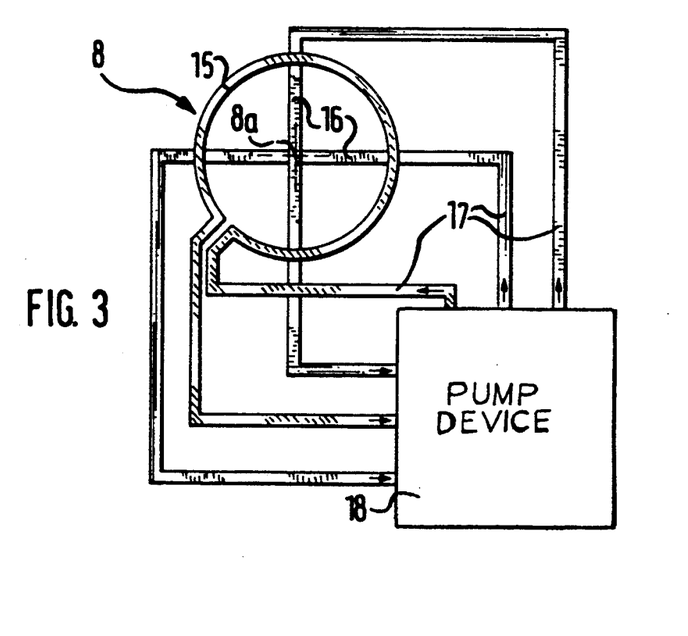
FIG. 3 shows a system for operating the spot film device according to FIG. 2.

FIGS. 2 and 3 show a first embodiment of the spot film device 8. It comprises two discs 12 and 13 of X-ray negative material, for example perspex, arranged parallel to one another, at a distance from one another and provided in the lower end region of the X-ray cone 4, and spot film markers 15, 16 of X-ray positive material. The spot film markers 15, 16 may consist, for example of channels, which are designed within the discs 12, 13 and represent geometrical figures, such that the course and the position of an intended spot film line 8a is defined by these figures, which spot film line 8a coincides with the central longitudinal axis 4a of the X-ray cone 4, which in turn, as already mentioned, coincides with the central axis 3 of the shock wave generator 2. However, the latter need not necessarily be the case, as FIG. 8 shows, if it is certain that the axis 4a of the X-ray cone 4 extends through the focus of the short wave generator 2.

In the example shown in FIG. 3 the geometrical figures of the spot film markers consist of a circle 15 for the upper disc 12 and a cross 16 for the lower disc 13. This can be seen clearly in FIG. 3. A circle may also be provided instead of a cross. Furthermore, other figures may also be provided for the spot film markers. It is also possible to see that the channels representing the spot film markers 15 and 16 are connected to a pump device 18 via pipes 17 for supplying and removing the X-ray positive liquid.

The X-ray positive liquid is pumped into the channels forming the spot film markers 15, 16 when the X-ray emitter 11 of the X-ray device 9 is to be aligned with the X-ray cone 4 and X-ray location of the object for therapy is to be carried out. The spot film line 8a is preset by the spot film device 8 so that the X-ray emitter 11 may be adjusted quickly and simply for this, that is the center of the ray bundle from the X-ray emitter is brought into alignment with the spot film line 8a or the central longitudinal line 4a of the X-ray cone 4 and hence is aligned with the focus of the shock wave generator.

The X-ray positive liquid may consist of a known X-ray contrast agent or even a mixture of alcohol and an X-ray contrast agent. Mercury may also be used as a further alternative, the thermometer principle being utilised. The introduction and removal of mercury is thus preferably carried out by means of heating or cooling with the aid of a Peltier element.

By introducing and removing the X-ray positive liquid again into or out of the channels, in use the spot film markers 15, 16 are, as it were, inserted into the X-ray cone 4 or their X-ray visibility is limited again afterwards. A suitable gas may also be used instead of a liquid for the X-ray positive material.

Figure 4:
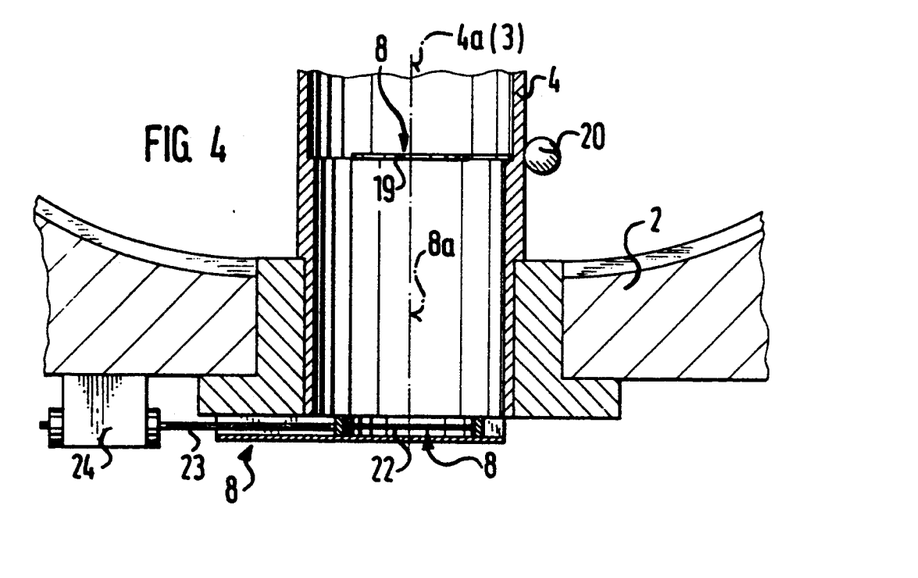
FIG. 4 shows an axial, enlarged partial section of a second embodiment of the spot film device.
Figure 5:
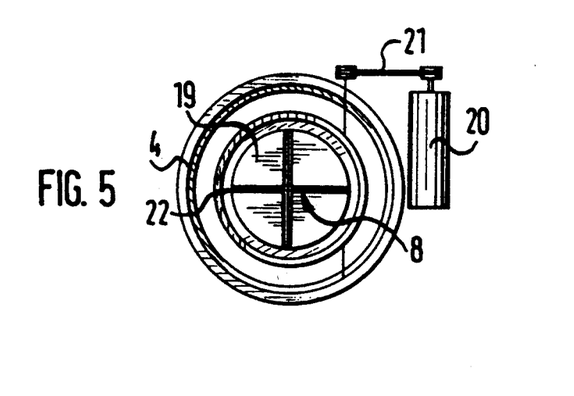
FIG. 5 shows a plan view of the representation according to FIG. 4.

A mechanical spot film device 8 is shown in FIGS. 4 and 5. FIG. 4 shows that a metal ring 19 is provided as a first spot film marker in the lower end region of the X-ray cone 4, the central point of the first spot film marker coinciding with the longitudinal axis 4a of the cone 4, and the metal ring 19 being designed to be rotatable about a horizontal axis according to FIG. 4. For this a motor 20, which effects pivoting of the metal ring 19 via a traction mechanism drive 21, is provided outside the cone 4. A metal part 22 in the form of a spot film cross is provided on the lower end of the cone 4 as a second spot film marker which can be adjusted horizontally and varied by means of a drive rod 23 using a lifting device 24, for example a lifting magnet. Hence, these spot film markers 19 and 22 can also be given greater at more limited X-ray visibility, as required. The two spot film markers 19 and 22 are also at a distance from one another and arranged to be parallel to one another in this case and form geometrical spot film figures of the required shape.

FIG. 6 shows that the therapy apparatus 1 is mounted pivotably on a frame 27 by means of an arm 25 about a horizontal axis 26. The horizontal axis 26 extends through the focus 28 of the shock wave generator 2. The coupling balloon of the short wave generator 2 is designated 29. The balloon 29 is shown to be expanded in the left part of the FIG. 6 drawing of the shock wave generator 2. Likewise, the patient operating table 30 is shown in a lowered position in the left and right parts of FIG. 6, respectively and in an elevated position.

Figure 7:
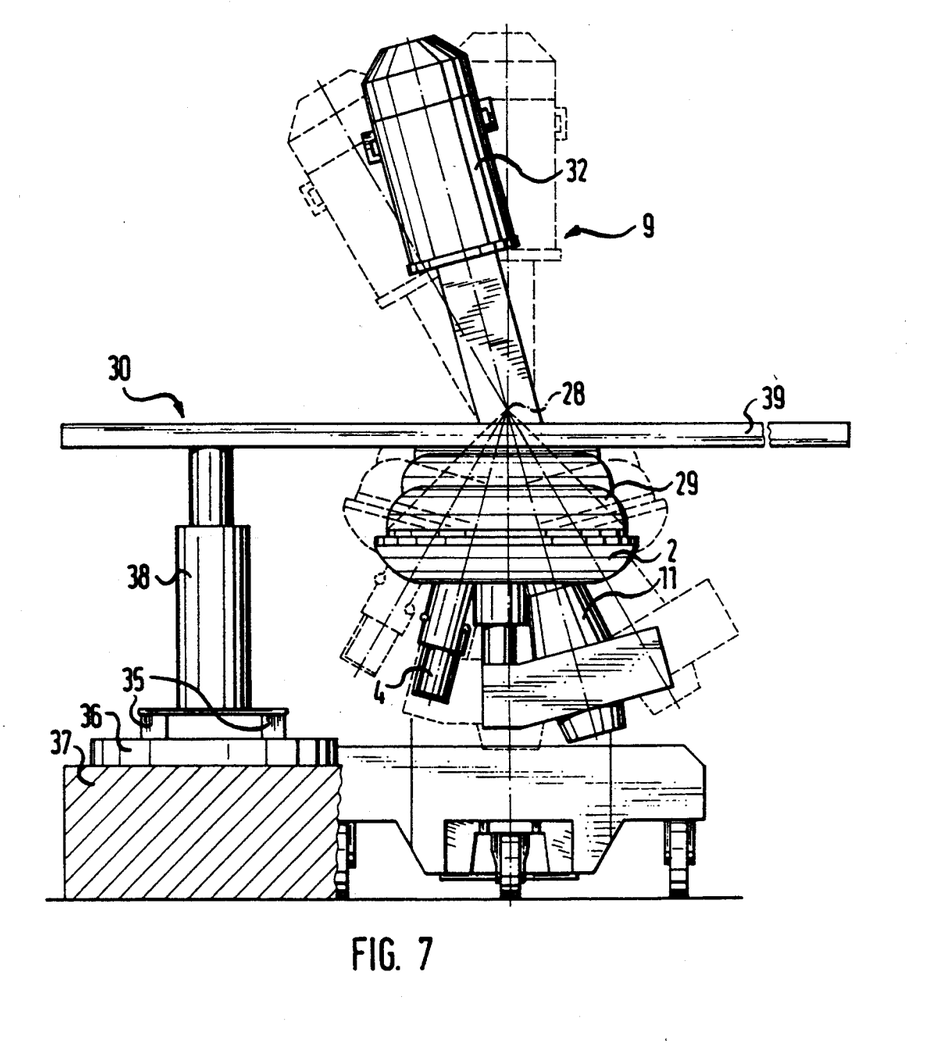
FIG. 7 shows a side view of the whole device along the arrow A in FIG. 6.

The available X-ray device 9 comprises a C-shaped support arm 31, one end of which carries the X-ray emitter 11 mentioned before and the other end of which has an image enhancer 32 axially aligned with the X-ray emitter 11 as shown in FIG. 7. The C-shaped support arm 31 is height-adjustable along the double arrow 33. In the case shown the X-ray device 9 is adjusted so that its horizontal pivoting axis 34 coincides with the horizontal pivoting axis 26 of the shock wave generator 2. Hence, the pivoting axis 34 also extends through the focus 28 of the short wave generator 2, as a result of which the X-ray device 9 can also be pivoted confocally about the focus 28.

The patient operating table 30 can be seen most clearly in FIG. 7. This table 30 can be adjusted in conventional manner in the three spatial coordinates X, Y and Z indicated in FIG. 6. The adjusting device for this comprises two upper and lower, surface-forming locating units 35 and 36 which can be adjusted in the horizontal X-Y coordinates and which rest on a base 37, and a lifting unit 38 arranged on the upper unit 35 and which is connected to the table plate 39 at the top. The construction of this adjusting device, that is the arrangement of the units 35, 36 in the flat plane below the lifting unit 38, makes it possible to provide a relatively thinly designed table plate 29 and this produces enlarged clearance below the table plate 29. This produces in turn a greater pivoting angle range for the therapy apparatus below the table plate 39.

FIG. 8 shows that the X-ray cone 4 may also be arranged out of, rather than in, in accordance with the central axis 3 of the shock wave generator 2. Its central longitudinal axis 4a is situated at an angle to the shock wave generator axis 3. In addition, a further location apparatus 40, which operates by in accordance with the continuous ultrasound location principle, may be provided. This apparatus 40 is arranged with its longitudinal axis also at an angle to the central axis 3. Cranial/caudal X-ray location is also possible using this design of therapy apparatus having an additional ultrasound location system 40, for example at an angle of 15° to the central axis 3.

Figure 9:
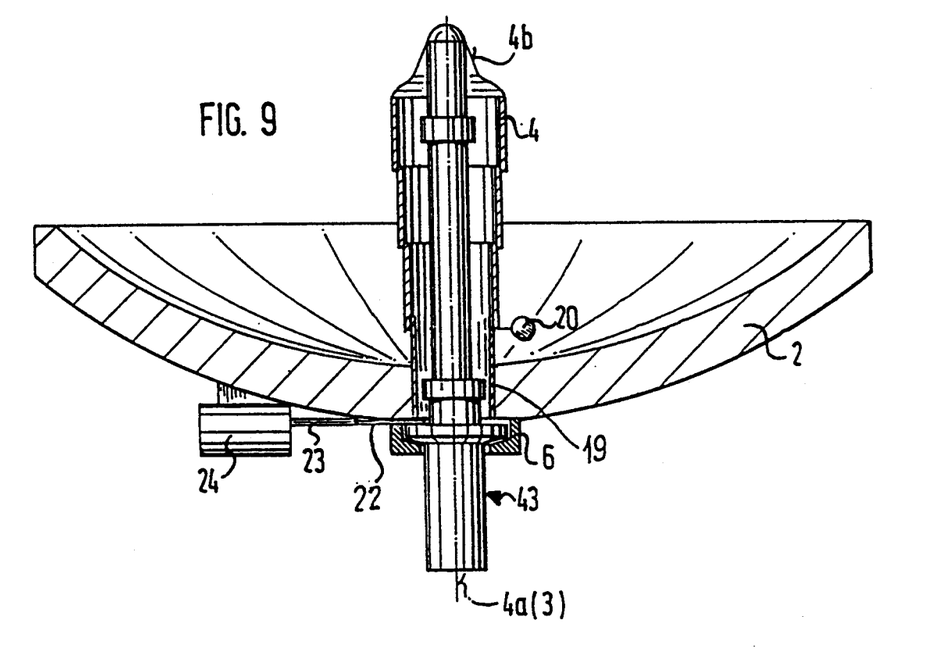
FIG. 9 shows a further, simplified axial section through a shock wave generator further equipped with ultrasound location device in the X-ray cone.

FIG. 9 shows a modified embodiment of the therapy apparatus for locating an object for therapy. Ultrasound location may be used instead of X-ray location. For this the X-ray device 9, the plate part 7 are removed and the spot film device 8 (FIG. 1) can be removed and an ultrasound location scanner 43 is inserted in the X-ray cone 4 and assembled on the mounting part 6. The scanner 43 can be rotated on the mounting part 6 that is mounted around it and is height-adjustable and in the direction of the longitudinal axis 4a of the X-ray cone 4. These movements may be executed by a motor. The X-ray cone 4 has a flexible sealing part 4b made of, for example, latex. The scanner 43 is coupled to the patient in terms of ultrasound by means of a gel composition. After ultrasound location of the object for therapy is completed, the treatment of the object, for example a tissue, is carried out by means of the ultrasound short wave generator 43.

The present invention may be embodied in other specific forms without departing from the spirit or essential attributes thereof and, accordingly, reference should be made to the appended claims rather than to the foregoing specification as indicating the scope of the invention.

We claim:

1. Extracorporeal therapy apparatus for treating concretions and tissue by means of sound waves in the body of a patient, comprising generator means for producing sound waves and directing them toward a focus, a spot film device, an X-ray device for locating an object for therapy, an X-ray cone attached to the generator means and bounding a passage having a central longitudinal axis aimed at said focus, means for supporting the spot film device in the passage in alignment with the central longitudinal axis thereof, means for releasably coupling the X-ray device with the generator means in substantial alignment with the central longitudinal axis, and means for mounting the generator means and the X-ray device for joint angular movement about said focus.

2. Therapy apparatus according to claim 1, wherein the spot film device comprises two discs of X-ray negative material arranged parallel to one another and at a distance from one another in the passage of the X-ray cone and spot film markers of X-ray positive material provided on the discs.

3. Therapy apparatus according to claim 2, wherein the spot film markers consist of channels representing geometrical figures formed in the discs, and of an X-ray positive liquid which can be pumped through the channels.

4. Therapy apparatus according to claim 3, wherein the X-ray positive liquid is an X-ray contrast agent, mercury or a mixture of alcohol and an X-ray contrast agent.

5. Therapy apparatus according to claim 2, wherein the center of the discs lie on the central axis of the X-ray cone.

6. Therapy apparatus according to claim 1, wherein the spot film device comprises two geometrically shaped spot film figures of solid X-ray positive material at a distance from one another and parallel to one another.

7. Therapy apparatus according to claim 6, wherein the spot film figures consist of metal components, and wherein said support means includes means for mounting the metal components for pivoting in and out of a ray path of the X-ray device passing through the X-ray cone.

8. Therapy apparatus according to claim 1, wherein said generator means includes a shock wave generator including a dome component having an axis passing through a center thereof and through said focus, wherein the X-ray cone is affixed in the center of the dome component such that a spot film line of the spot film device extends through said focus of the shock wave generator.

9. Therapy apparatus according to claim 1, further comprising a patient operating table including a table plate and means for adjusting the table plate in three spatial coordinates, said adjusting means including two lower locating units which are adjustable in horizontal X-Y-coordinates and a lifting unit provided so as to support the table plate arranged thereon.

10. Therapy apparatus according to claim 1, wherein said generator means includes a shock wave generator including a dome component having an axis passing through a center thereof and through said focus, wherein the X-ray cone is affixed to said shock wave generator at an angular offset of said central longitudinal axis thereof from said axis of said dome component such that a spot film line of the spot film device extends through said focus of the shock wave generator.

11. An extracorporeal therapy kit for treating concretions and tissue in the body of a patient by means of sound waves, comprising: generator means for producing sound waves and directing them toward a focus; a spot film device; an X-ray device for locating an object for therapy; an X-ray cone attached to the generator means and bounding a passage having a central longitudinal axis aimed at said focus; an ultrasound scanner for ultrasound location of the object for therapy; means for removably supporting the spot film device in the passage in alignment with the central longitudinal axis thereof; means for interchangeably and releasably coupling the X-ray device and the ultrasound scanner with the generator means in substantial alignment with the central longitudinal axis; means for mounting the generator means, the X-ray device and the ultrasound scanner for joint angular movement about said focus; and, a motor for rotating the ultrasound scanner and adjusting the ultrasound scanner along the longitudinal axis of the X-ray cone.

* * * * *